(12) United States Patent
Ruffa

(10) Patent No.: US 9,316,604 B1
(45) Date of Patent: Apr. 19, 2016

(54) METHOD AND APPARATUS FOR NON-DESTRUCTIVELY DETERMINING FEATURES IN A PLANAR SPECIMEN

(71) Applicant: Anthony A. Ruffa, Hope Valley, RI (US)

(72) Inventor: Anthony A. Ruffa, Hope Valley, RI (US)

(73) Assignee: The United States of America as represented by the Secretary of the Navy

(*) Notice: Subject to any disclaimer, the term of this patent is extended or adjusted under 35 U.S.C. 154(b) by 271 days.

(21) Appl. No.: 14/162,017

(22) Filed: Jan. 23, 2014

(51) Int. Cl.
*G01N 25/00* (2006.01)
*G01N 25/72* (2006.01)
*G01N 25/18* (2006.01)

(52) U.S. Cl.
CPC .................................... *G01N 25/18* (2013.01)

(58) Field of Classification Search
CPC ................................ G01N 25/00; G01N 25/72
USPC ............................................................. 374/45
See application file for complete search history.

(56) References Cited

U.S. PATENT DOCUMENTS

| 6,906,801 | B2* | 6/2005 | Borden | G01N 21/1717 257/E21.53 |
| 6,958,814 | B2* | 10/2005 | Borden | G01N 27/041 356/237.2 |
| 2011/0142091 | A1* | 6/2011 | Wardle | B82Y 15/00 374/45 |
| 2014/0095096 | A1* | 4/2014 | Na | G01N 25/72 702/81 |
| 2015/0253266 | A1* | 9/2015 | Lucon | G01N 25/72 374/4 |

* cited by examiner

*Primary Examiner* — Lisa Caputo
*Assistant Examiner* — Jamel Williams
(74) *Attorney, Agent, or Firm* — James M. Kasischke; Michael P. Stanley

(57) ABSTRACT

A method and apparatus for non-destructively determining features in a planer specimen includes providing a heat impulse to the specimen, detecting temperatures in the specimen at a plurality of locations, and imaging the specimen from the detected temperatures. A laser can be used to provide a single or a plurality of heat impulses to the specimen. Temperatures in the specimen can be detected utilizing a contact sensor array or a remote infrared detector. These sensors are joined to a data processing device to image the specimen utilizing the detected temperatures.

15 Claims, 2 Drawing Sheets

METHOD AND APPARATUS FOR NON-DESTRUCTIVELY DETERMINING FEATURES IN A PLANAR SPECIMEN

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention is directed to non-destructive testing and more particularly to a method for detecting microscopic structures within a specimen.

(2) Description of the Prior Art

Optical microscopes are commonly used to discern small features embedded in specimens. Electron microscopes are also used to discern small features which can be imaged. Electron microscopes exhibit a significantly lower diffraction limit than optical microscopes because the wavelengths of electron beams are much smaller than wavelengths of light. However, electron microscopes are much more expensive than optical microscopes and further require that the specimens be tested in a vacuum.

Photothermal frequency scan imaging is used for materials analysis in semiconductor manufacture. In photothermal frequency scan imaging a sample is subjected to a pulsed laser. This can be used to detect surface conditions of the sample, but it has only been found to be effective for a limited depth in the sample. These methods have had problems with internal reflections in smaller samples. These methods have also been used as an indication of homogeneity within a sample and also for determining thermal properties within the sample. These methods have not been used to image individual discontinuities within a sample.

SUMMARY OF THE INVENTION

Accordingly, it is an object of the present invention to provide a method and apparatus for detecting features embedded in specimens;

Another object is to provide method and apparatus that can detect features without subjecting the specimen to vacuum; and Yet another object is to provide a method and apparatus that can detect features without expensive equipment.

In view of these objects, there is provided a method and apparatus for non-destructively determining features in a planar specimen that includes providing a heat impulse to the specimen, detecting temperatures in the specimen at a plurality of locations, and imaging the specimen from the detected temperatures. A laser can be used to provide a single or a plurality of heat impulses to the specimen. Temperatures in the specimen can be detected utilizing a contact sensor array or a remote infrared detector. These sensors are joined to a data processing device to image the specimen utilizing the detected temperatures.

BRIEF DESCRIPTION OF THE DRAWINGS

Reference is made to the accompanying drawings in which are shown an illustrative embodiment of the invention, wherein corresponding reference characters indicate corresponding parts, and wherein.

DETAILED DESCRIPTION OF THE INVENTION

Figure 1:
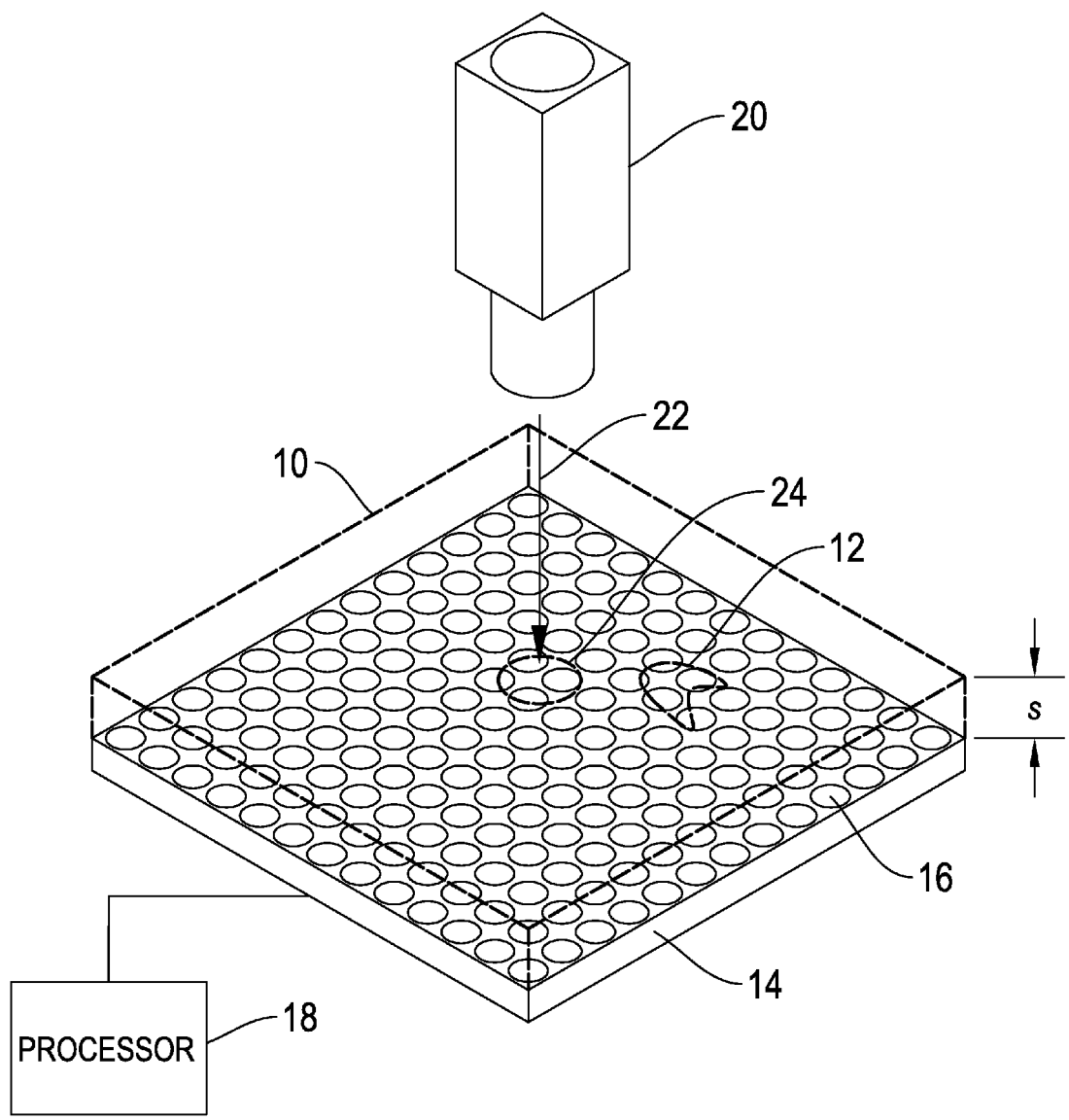
FIG. 1 is a diagrammatic view of one method illustrative of an embodiment of the invention.
Figure 2:
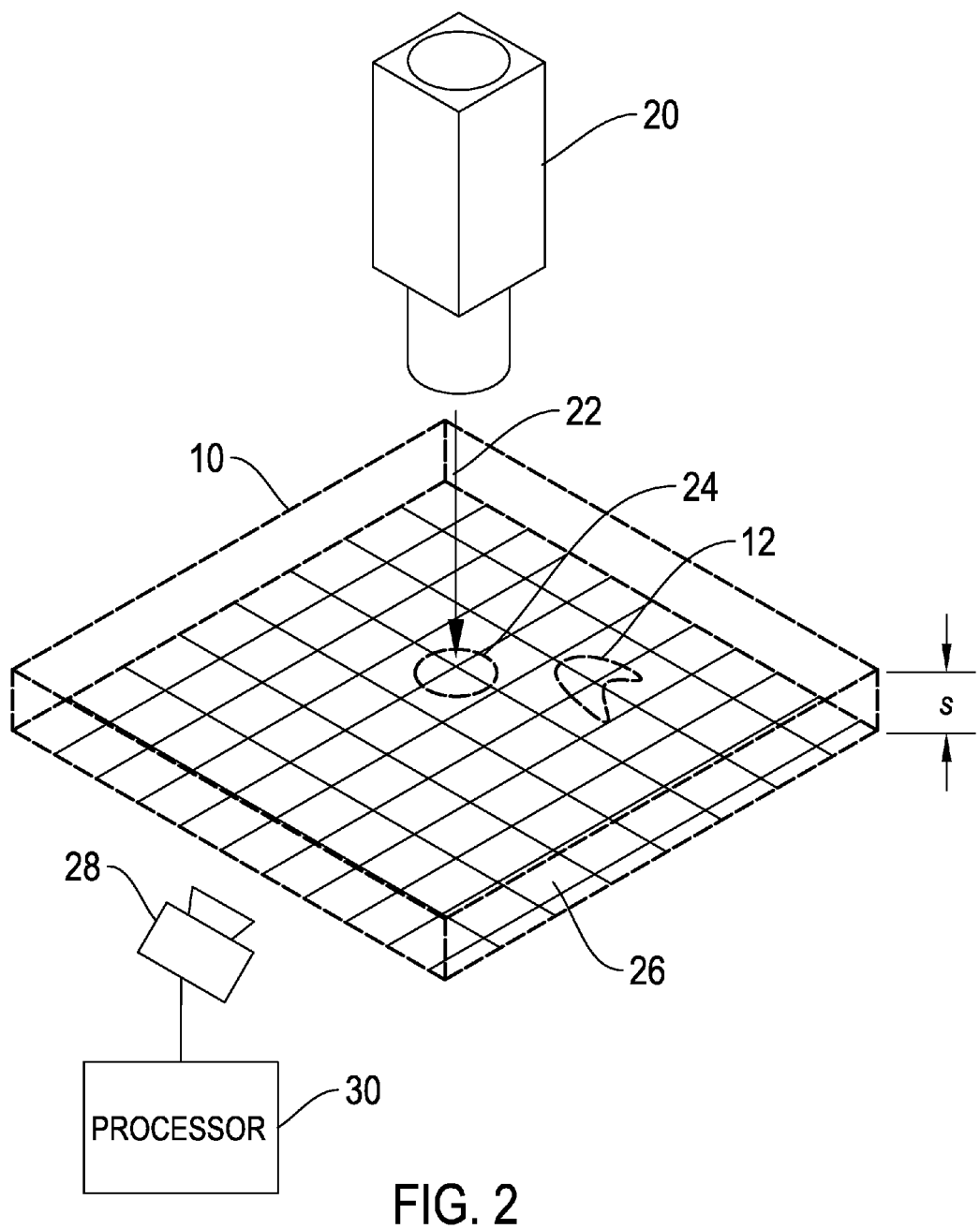
FIG. 2 is a block diagram further illustrative of the embodiment of FIG. 1.

The transient conduction of heat is typically treated as a diffusion process; however, if the heat source is periodic in nature, heat can propagate in a wavelike manner. This can be shown by examining the one-dimensional transient heat conduction equation:

$$\frac{\partial T}{\partial t} = \alpha \frac{\partial^2 T}{\partial x^2} \tag{1}$$

wherein $\alpha$ is the thermal diffusivity; T is the temperature; t is time; and x is the spatial dimension. If the temperature has a harmonic time dependence (e.g., as a result of a pulsed laser) then:

$$T(x,t) = \tau(X)e^{-i(\omega t - kx)} \tag{2}$$

wherein $\omega = 2\pi f$ (and f is the pulse frequency), then equation (1) can be written in the form:

$$i\omega\tau = \alpha \frac{\partial^2 T}{\partial x^2} \tag{3}$$

having the solution:

$$T(x,t) = T_0 e^{i(\omega t - kx)} \tag{4}$$

where:

$$k = \omega/c = \sqrt{-i\omega/\alpha} \tag{5}$$

The above solution for T(x,t) is analogous to the solution to the acoustic wave equation. However, the propagation speed of these temperature waves is much slower than that of acoustic waves. (Temperature waves propagate at 10 m/s and acoustic waves propagate at 5,000 m/s for most solids.) Attenuation is also much higher for temperature waves than for acoustic waves.

Use of temperature waves gives advantages and disadvantages when compared with other types of radiation. Temperature waves are distinct from infrared (IR) waves, which propagate at the speed of light. Many materials block infrared waves, but even if the infrared waves are not blocked, their wavelengths are much longer than those of the temperature waves and 10 nanometer resolution is impossible. Infrared sensors thus receive the same signal in each closely spaced sensor.

The formula for the wavenumber equation (5) implies that the propagation speed $c = \sqrt{i\omega\alpha}$ varies with the radial frequency, $\omega$. This means that the propagation speed associated with the higher-frequency energy travels at a faster speed than that of the lower-frequency energy. This can enable "time gating" of the signals that arrive at the thermistor array first to image features based on the highest frequency energy contained in a pulse. The highest frequency energy will also have the shortest wavelength. Significant high-frequency energy can be contained by a single, very short duration pulse. A pulse having a time duration $\Delta T$ will contain significant energy at a frequency, $f=1/(\Delta T)$.

For many thermally insulating materials, the thermal diffusivity, $\alpha$, is on the order of $10^{-8}$ m$^2$/s. Thus, using the above equations, it can be shown that a laser sending a pulse having a duration, $\Delta T$, of 10 ns would lead to a wavelength on the order of 10 nm. This is better than the diffraction limit of optical microscopes. It can be improved upon further with a femtosecond pulse laser, which would lead to a wavelength on the order of 1 nm. This is two orders of magnitude larger than the diffraction limit that can be achieved with electron microscopes. This method also avoids some of the negative features associated with electron microscopes, e.g., their high cost and the necessity of putting the specimen into a vacuum.

FIG. 1 shows a specimen 10 positioned for analysis according to a first embodiment. Specimen 10 has possible discontinuities 12 therein and a thickness given at s. An array 14 of thermal sensors is positioned in thermal contact with a first side of specimen 10. A single thermal sensor of array 14 is identified at 16. Thermal sensors 16 can be thermistors or thermocouples and can also be realized as micro-electromechanical system (MEMS) components. These sensors should be spaced from each other by at most one half wavelength of the temperature waves. Sensors 16 and array 14 can be electrically joined to a processor 18 to allow the processor 18 to image the specimen 10 from temperature variations at the sensors 16. Heat is applied to specimen 10 by a pulsed laser 20. Pulsed laser 20 is capable of providing a single pulse of light or multiple pulses as indicated by arrow 22 to a target location 24 on specimen 10. Multiple pulses are provided at a known pulse width $\Delta T$ and pulse frequency, f. The frequency or color of the light in the pulse does not greatly affect heat transfer to the specimen. Thus, it is more important to select the laser based on the pulse frequency rather than the color of light.

In operation, pulsed laser 20 provides pulses of light 22 to target location 24 on specimen 10. Pulses of light 22 cause an increase in temperature at target location 24. The temperature increase propagates to adjacent regions of specimen 10 by well-known heat transfer principles. Sensors 16 of array 14 measure the temperature of specimen 10 at the region of contact with the sensor. The temperature waves propagating through the specimen will interact with discontinuity 12 and propagate to the sensor array contact surface of the specimen 10. Processor 18 collects the temperature measurements and provides an output indicative of temperature propagation through specimen 10. Processor 18 can time gate the array 14 output to prevent spurious signals caused by reflection of the temperature waves.

In a second embodiment, temperature is measured at a multiplicity of locations 26 on the first surface of specimen 10 by an infrared temperature detector 28. Infrared temperature detector 28 can be scanned across first surface to measure temperature at each location 26 to be measured. Infrared temperature detector 28 can be an infrared camera that images the entire first surface of specimen 10 at once. Infrared temperature detector 28 is joined to a processor 30 for analysis. Using an infrared detector doesn't have the same limitations as trying to measure infrared propagation through the material; however, the detector 28 must have sufficient resolution and precision to measure locations at intervals no greater than one half wavelength of the temperature waves.

This approach has the potential to resolve features on the order of nanometers, giving a much higher resolution than that of optical microscopes. The specimen, however, must have a thickness no more than about 10 wavelengths of the temperature waves. For example, temperature waves from a 1 ns pulse duration have a $1/\Delta T$ frequency, $f=1$ GHz, and have propagation speed, c, through a typical specimen of about 10 m/s. Using the wave equation:

$$\lambda = c/f \qquad (6)$$

gives a wavelength of 10 nm. Using equation (5) the wave number, $k=2\pi 10^8 \sqrt{-i} = 2.22*10^8(-1+i)$. Based on this, the original temperature signal will decay to 1/e in approximately $10^{-8}$ m. Depending on the sensitivity of the thermal array, the specimen can have thickness s of up to $10\lambda$ or 100 nm.

There is thus provided a method for non-destructivity determining features embedded in a planar specimen, which method is inexpensive, requires minimal sample preparation, can resolve differences in thermal properties (e.g., thermal diffusivity), which in some cases means resolving differences in material composition, and can have a very low diffraction limit (based on the laser pulse frequency), because of the slow propagation speed.

It will be understood that many additional changes in the details, materials, steps and arrangement of parts, which have been herein described and illustrated in order to explain the nature of the invention, may be made by those skilled in the art within the principle and scope of the invention as expressed in the appended claims.

The foregoing description of the preferred embodiments of the invention has been presented for purposes of illustration and description only. It is not intended to be exhaustive, nor to limit the invention to the precise form disclosed; and obviously, many modification and variations are possible in light of the above teaching. Such modifications and variations that may be apparent to a person skilled in the art are intended to be included within the scope of this invention as defined by the accompanying claims.

What is claimed is:

1. A method for non-destructively determining features embedded in a planar specimen comprising the steps of:
   propagating at least one heat wave onto an exposed surface of the specimen whereby the heat wave travels through the specimen;
   measuring temperatures at an opposite surface of the specimen after propagation of said at least one heat wave; and
   utilizing said measured temperatures in a data processing device to image the specimen to determine internal features of the specimen.

2. The method of claim 1 wherein said step of propagating at least one heat wave comprises propagating periodic pulses of heat waves onto the exposed surface of the specimen, said periodic pulses having a duration and a frequency resulting in a temperature wave propagation wavelength.

3. The method of claim 2 wherein the frequency is at least 100 MHz.

4. The method of claim 2 further comprising the step of preparing the specimen with a thickness of less than ten temperature propagation wavelengths.

5. The method of claim 1 wherein said step of propagating at least one heat wave comprises propagating a single very short duration pulse onto the exposed surface of the specimen, said pulse having significant high-frequency energy that generates a temperature wave propagation wavelength.

6. The method of claim 1 further comprising the step of providing an array of temperature sensors in contact with an opposite surface of the specimen and joined to the data processing device wherein said step of measuring temperatures is performed by said array of temperature sensors.

7. The method of claim 6 wherein said step of propagating at least one heat wave comprises propagating periodic pulses of heat waves onto the exposed surface of the specimen, said periodic pulses having a duration and a frequency resulting in a temperature wave propagation wavelength, and each sensor of said array of temperature sensors is positioned within one half temperature propagation wavelength of another sensor.

8. The method of claim 1 further comprising the step of providing an infrared temperature detector proximate an opposite surface of the specimen and capable of measuring temperatures at a plurality of locations on said opposite surface, and said infrared temperature detector being operatively joined to the data processing device wherein said step of measuring temperatures is performed by said infrared temperature detector.

9. The method of claim 8 wherein said step of propagating at least one heat wave comprises propagating periodic pulses of heat waves onto the exposed surface of the specimen, said periodic pulses having a duration and a frequency resulting in a temperature wave propagation wavelength, and said infrared temperature detector is capable of measuring temperatures at locations within one half temperature propagation wavelength of each other.

10. A device for non-destructively imaging features in a planar specimen comprising:
   a laser positioned to provide light to heat a region on an exposed surface of the specimen;
   a means for measuring temperatures at a plurality of locations on an opposite surface of the specimen; and
   a data processing system joined to the means for measuring temperatures for receiving temperatures and providing an image of the internal structure of the specimen.

11. The device of claim 10 wherein said laser provides periodic pulses of light at the region on the exposed surface of the specimen, said periodic pulses having a duration and a frequency resulting in a temperature wave propagation wavelength.

12. The device of claim 11 wherein said laser is capable of providing periodic pulses of light at a frequency greater than 100 MHz.

13. The device of claim 10 wherein said means for measuring temperatures comprises an array of temperature sensors in contact with an opposite surface of the specimen and joined to said data processing device for measuring temperatures at the plurality of locations.

14. The device of claim 13 wherein each temperature sensor of said array of sensors is a MEMS device.

15. The device of claim 10 wherein said means for measuring temperatures comprises an infrared temperature detector proximate the opposite surface of the specimen and capable of measuring temperatures at the plurality of locations on said opposite surface, and said infrared temperature detector being operatively joined to the data processing device.

* * * * *